(12) United States Patent
Bulut et al.

(10) Patent No.: US 10,216,900 B2
(45) Date of Patent: Feb. 26, 2019

(54) MONITORING INFORMATION PROVIDING DEVICE AND METHOD

(71) Applicant: KONINKLIJKE PHILIPS N.V., Eindhoven (NL)

(72) Inventors: Murtaza Bulut, Eindhoven (NL); Charles Frederik Sio, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 554 days.

(21) Appl. No.: 14/857,924

(22) Filed: Sep. 18, 2015

(65) Prior Publication Data
US 2016/0103967 A1 Apr. 14, 2016

(30) Foreign Application Priority Data
Oct. 13, 2014 (EP) ..................................... 14188673

(51) Int. Cl.
*G06F 19/00* (2018.01)
*G16H 40/63* (2018.01)
*G16H 50/20* (2018.01)
*G16H 20/10* (2018.01)
*A61B 5/00* (2006.01)
(Continued)

(52) U.S. Cl.
CPC ............ *G06F 19/321* (2013.01); *G06F 19/00* (2013.01); *G16H 20/10* (2018.01); *G16H 40/63* (2018.01); *G16H 50/20* (2018.01); *A61B 5/021* (2013.01); *A61B 5/024* (2013.01); *A61B 5/411* (2013.01); *A61B 5/7275* (2013.01); *A61B 5/746* (2013.01)

(58) Field of Classification Search
CPC .............................. G06Q 50/22; G06Q 50/24
See application file for complete search history.

(56) References Cited

U.S. PATENT DOCUMENTS 8,145,590 B2  3/2012  Brockway et al.
8,454,507 B2  6/2013  Tremper et al.
(Continued)

FOREIGN PATENT DOCUMENTS

WO  2011112972 A2  9/2011
WO  2014091329 A1  6/2014

OTHER PUBLICATIONS

Koutkias, V. G., et al.; A Personalized Framework for Medication Treatment Management in Chronic Care; 2010; ' IEEE Trans. on Information Technology in Biomedicine; 14(2)464-472.

*Primary Examiner* — Jonathan Ng (57) ABSTRACT

Information regarding a patient's physiological signs is provided in real-time, in particular in conjunction with drug administration to the patient. A patient data input obtains patient data of a monitored patient. A drug identification input obtains drug administration data identifying a drug administered to the patient and the time of administration of the drug to the patient. A drug information input obtains drug information about the identified drug, including drug side effects and/or drug-drug interactions and/or drug-disease contraindications. A processing unit determines time-resolved monitoring information based on the obtained patient data, drug administration data and drug information. The monitoring information is dynamically adapted and one or more physiological signs of the patient that are most critical to monitor over time are indicated. An output interface outputs the monitoring information.

20 Claims, 5 Drawing Sheets

(51) Int. Cl.
*A61B 5/021* (2006.01)
*A61B 5/024* (2006.01)

(56) References Cited

U.S. PATENT DOCUMENTS

| | | |
|---|---|---|
| 2003/0083557 A1 | 5/2003 | Schmidt |
| 2006/0009478 A1* | 1/2006 | Friedmann ............ A61K 31/485 |
| | | 514/282 |
| 2007/0219823 A1 | 9/2007 | Warner |
| 2007/0244724 A1 | 10/2007 | Pendergast et al. |
| 2008/0109260 A1* | 5/2008 | Roof ................... G06F 19/3456 |
| | | 705/3 |
| 2009/0036757 A1* | 2/2009 | Brockway ............ A61B 5/0002 |
| | | 600/301 |
| 2010/0137786 A1* | 6/2010 | Alferness ............ G06F 19/3437 |
| | | 604/66 |
| 2010/0145670 A1* | 6/2010 | Alferness ............ G06F 19/3437 |
| | | 703/11 |
| 2012/0116194 A1* | 5/2012 | Gross ...................... A61B 5/00 |
| | | 600/324 |
| 2013/0245502 A1 | 9/2013 | Lange |

\* cited by examiner

MONITORING INFORMATION PROVIDING DEVICE AND METHOD

CROSS REFERENCE TO RELATED APPLICATIONS

This application is claims the benefit of EP provisional application serial no. 14188673.9 filed Oct. 13, 2014, which is incorporated herein by reference.

FIELD OF THE INVENTION

The present invention relates to a monitoring information providing device and a corresponding monitoring information providing method.

BACKGROUND OF THE INVENTION

Patient monitoring devices (herein also called patient monitors), as often used in hospitals located next to the patient bed, are generally known in the art. They are used as a kind of measurement devices for measuring and displaying of physiological signs and for providing alarming and scoring based on the captured physiological signs. In case a caregiver decides to visit a patient, physiological signs, alarms and scores are available for review.

Conventional bedside patient monitors are able to measure and show the patient's physiological signs in real-time. They can also be connected to other devices, such as a PC, enabling caregivers to access and view all information available in the hospital database on a single screen.

U.S. Pat. No. 8,145,590 B2 discloses an expert system for patient medical information analysis. A plurality of chronic sensors is used to facilitate diagnosis and medical decision making for an individual patient. An expert system evaluates the sensor data, combines the sensor data with stored probability data and provides an output signal for notification or medical intervention.

WO 2014/091329 A1 discloses a monitoring apparatus for monitoring vital functions of a patient, comprising a connection device connectable to a patient medication storage unit and for receiving information about at least one drug administered to the patient, an interface connectable to a drug database for receiving information about at least one effect of the at least one administered drug and/or a combination of administered drugs, a measurement device associated to the patient for measuring at least one vital parameter of the patient, and a control unit for enabling a measurement of at least one vital parameter and/or for enabling an evaluation of a measurement of at least one vital parameter on the basis of the information about the at least one effect.

V. Koutkias et al., "A personalized framework for medication treatment management in chronic care", IEEE Transactions on Information Technology in Biomedicine, Special section on affective and pervasive computing for healthcare archive, Volume 14 Issue 2, March 2010, pages 464-472 discloses a framework for monitoring the patient's condition and safety with respect to the medication treatment administered. For this purpose, considering a body area network (BAN) with advanced sensors and a mobile base unit as the central communication hub from the one side, and the clinical environment from the other side, an architecture is described, offering monitoring patterns definition for the detection of possible adverse drug events and the assessment of medication response, supported by mechanisms enabling bidirectional communication between the BAN and the clinical site.

SUMMARY OF THE INVENTION

It is an object of the present invention to provide a monitoring information providing device and a corresponding monitoring information providing method which provide more information regarding a patient's physiological signs in real-time, in particular in case of a drug administration to the patient.

In a first aspect of the present invention a monitoring information providing device is presented comprising:
  a patient data input for obtaining patient data of a monitored patient,
  a drug identification input for obtaining drug administration data identifying a drug administered to the patient and the time of administration of the drug to the patient,
  a drug information input for obtaining drug information of the identified drug, said drug information including drug side effects and/or drug-drug interactions and/or drug-disease contraindications,
  a processing unit for determining time-resolved monitoring information based on the obtained patient data, drug administration data and drug information, said monitoring information being dynamically adapted and indicating one or more physiological signs of the patient that are most critical to monitor over time, and
  an output interface for outputting said monitoring information.

The steps performed by the inputs, the processing unit, and the output interface can be performed with one or more processors.

In a further aspect of the present invention a corresponding monitoring information providing method is presented comprising with one or more processors:
  obtaining patient data of a monitored patient,
  obtaining drug administration data identifying a drug administered to the patient and the time of administration of the drug to the patient,
  obtaining drug information of the identified drug, said drug information including drug side effects and/or drug-drug interactions and/or drug-disease contraindications,
  determining time-resolved monitoring information based on the obtained patient data, drug administration data and drug information, said monitoring information being dynamically adapted and indicating one or more physiological signs of the patient that are most critical to monitor over time, and
  outputting said monitoring information.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

The present invention is based on the idea to adapt and/or highlight the real-time physiological signs information that is outputted, e.g. shown on a display of a patient monitor, based on drug information. From pharmacology it is known that the drug distribution in body, and consequently the expected effects in terms of physiological signs, depends on absorption and distribution to the site of action. As such, the onset of adverse effects will depend on the administration route (e.g. tablet or intravenous injection) and the affected organ (e.g. a drug in an oral formulation will affect the stomach quickly but the kidneys much later).

There are several factors that may affect the drug effects in body, and they may be accounted for when predicting the possible changes in physiological signs. These factors include current patient condition, disease and allergies, renal, hepatic and cardiac function, dose and time of last dose, genetics, age, weight, gender, drug-drug interactions, diet and activity. According to the present invention at least the kind of drug and the exact time, and preferably also route, of drug administration is obtained and used to determine the expected changes in physiological signs in a time-resolved manner.

Adverse effects of drugs due to side effects, drug-drug (or drug-food) interactions and contraindications are known to the specialists. However, not everyone is a specialist in this area, and therefore guidance is needed. The proposed monitoring information providing device and method support medical personnel towards the right information, so that they can improve the patient care by performing the appropriate checks and delivering the appropriate treatment quicker and more consistently. In a way the proposed device and method make quality of patient care less dependent on the knowledge level of the attending personnel, e.g. a nurse or a doctor. It promotes sharing relevant and up-to-date information quicker, and has the potential to minimize preventable errors in hospitals.

In contrast, conventional drug interaction monitoring systems and software are very generic. They do not provide any (in particular physiological signs and adverse effect) information about the timeline of expected drug effects, or drug-drug interactions, and what to monitor at what time. There is no prioritization of which physiological signs to monitor and at what times, based on expected drug effects or drug-drug interactions.

From drug effects, drug-drug interaction, drug-disease contraindication (e.g. obtained from a drug database, available at the hospital, pharmacy or other drug dispenser, the drug manufacturer or some other place accessible in any way from the monitoring information providing device, for instance via a communications system such as the internet) and patient data (e.g. obtained from patient history databases, such as an electronic health record (EHR) or electronic medical record (EMR) storing historic medical patient data), information about the most important physiological signs and adverse effects to monitor are available. Up to now, such information is rarely or not used, and in many settings (e.g. home situation) time of drug administration is not known to the healthcare professionals. For proper judgment of relevance both the time of drug administration and knowledge about the effects, adverse effects and effects on physiological signs should be known. In many cases, the knowledge is with a specialist, pharmacist or hospital pharmacist, but these people do not know the time of drug administration in a home situation.

This level of knowledge (related to expected drug effects, their time course and the effects on physiological signs) is generally not incorporated in known systems to check patient medication. This leads to the generation of many medication alert signals, which then have to be judged by the nurse, doctor and/or pharmacist for clinical relevance. In addition, there is little information on what to do if an interaction or contraindication is unavoidable or has already happened (e.g. in emergency situations). Adding the time of administration, as proposed by the present invention, leads to the generation of fewer medication alerts, which are of higher clinical relevance, and time-specific physiological signs to monitor whether a patient is experiencing a clinically relevant adverse effect.

It shall be noted that in the context of the present invention the term "physiological signs" shall be understood broadly as any signs that relate in any way to the physiology of the patient. The physiological signs include any kinds of vital signs, such as heart rate, blood pressure, respiration rate, SpO2, temperature, etc., but also other signs such as allergic skin reactions, dry mouth, dry eyes, which may also be relevant signs to monitor.

According to the present invention it is proposed to output dynamically adapted monitoring information, e.g. on a display of the monitoring information providing device, a separate display (e.g. of a patient monitoring device), a central surveillance monitor at a nurse station, etc., based on expected adverse reactions due to drug side effects, drug-drug interactions or drug-disease contraindications. The outputted information is time-resolved, which means that the data is updated following the time course of the potential adverse effects, and indicates the clinically most critical physiological signs to pay attention to, i.e. the physiological signs which are important for the particular patient's health state and which, when reaching a critical state, may indicate a serious adverse health state of the patient.

The monitoring information may include the physiological signs itself, but may instead or additionally only comprise a list or any other indication (e.g. highlighting) of physiological signs and conditions that are likely to be influenced and that are critical to monitor, without displaying the acquired signals or physiological signs derived there from.

The benefits of the present invention are that it makes (or emphasizes) the outputted physiological sign information more relevant to the patient's condition. In preferred embodiments this information may be used to prioritize alarms and/or adapt the alarm thresholds dynamically. In addition to outputting drug-related information, the proposed device and method may suggest and/or automatically initiate additional measurements such as blood pressure in a time-resolved manner, according to the times when blood pressure changes are expected and most relevant.

It shall be noted that in the context of the present application the expression "obtaining" shall be understood in a way that includes (actively) "collecting" or "fetching" as well as (passively) "receiving".

The proposed monitoring information providing device and method may be a stand-alone device and method, respectively, and may be implemented by e.g. a PC, processor or any other hardware comprising the respective means and suitable to carry out the respective steps. Alternatively, they may also be integrated into other devices and methods, e.g. into a patient monitor, a hospital workstation, a doctor's tablet or smartphone, a nurse's monitoring station, etc.

According to a preferred embodiment the processing unit is configured to determine monitoring information further indicating at what time changes of physiological signs are expected, to which extent changes are expected,
how critical the respective changes are,
which potential drug side effects, drug-drug interactions, drug-disease contraindications and/or drug-food interactions may appear, and/or
how these potential drug side effects, drug-drug interactions, drug-disease contraindications and/or drug-food interactions are expected to cause changes of physiological signs, to which extent changes are expected and/or how critical the respective changes are.

This further provides helpful information to a user, e.g. a caregiver, to pay attention to the right physiological signs and to avoid misinterpretations of (expected) changes of certain physiological signs with (potentially dangerous) worsening of the patient's condition or health state.

Further, not only information regarding the most critical physiological signs may be generated and outputted, but also information for which physiological signal changes are expected. For instance, if a patient is given drug A to lower blood pressure, the expected change is a drop in blood pressure. This is the intended change that staff is prepared for. This may be highlighted, but it does not have a higher priority, as it does not indicate a critical adverse reaction. On the contrary, the drug A may potentially induce atrial fibrillation as a side effect, in some cases. This is a critical parameter that needs a critical attention if it happens, and this one should be highlighted with a higher priority. This will further support understanding of the outputted information and of the changes of physiological signs as a response to the drug administration.

Preferably, the monitoring information providing device further comprises a control unit for generating control information for controlling one or more sensors, which provide sensor signals related to one or more physiological signs that have been determined to be most critical to monitor, to adapt the measurements made by the one or more sensors based on the determined monitoring information. For instance, said control unit is configured to generate control information for controlling one or more sensors to start measurement, to perform measurement for a particular time period, to change the measurement frequency and/or to adapt other settings of the measurement based on the determined monitoring information. Thus, preferably useful and required sensor signals are provided, which are both drug-related and patient-related and which provide an even further improved overview of the patient's real-time health status over time. The current sensor signals may also be continuously fed to the proposed device and method, e.g. via a sensor interface, to check and, if necessary, adapt the monitoring information.

In another embodiment said drug identification input is configured to obtain drug administration data further including the route of administration and/or the amount of the drug administered to the patient. It has been found that this information further improves the accuracy of the determination and dynamic adaption of the monitoring information.

In another embodiment said drug identification input is configured to obtain further drug administration data identifying one or more further drugs that have been administered earlier or that will be administered later to the patient and the time of administration of the one or more further drugs, wherein said processing unit is configured to use the further drug administration data in the determination of the monitoring information. Preferably, said drug identification input is configured to obtain further drug administration data further including the route of administration and/or the amount of the one or more further drugs. This again further improves the accuracy of the determination and dynamic adaption of the monitoring information.

In an embodiment the monitoring information providing device further comprises a sensor interface for obtaining one or more sensor signals related to one or more physiological signs of the patient, wherein said processing unit is configured to use the sensor signals in the determination of the monitoring information. This may further improve the accuracy of the monitoring information. The sensor signals may be inputted directly from the respective sensor (e.g. in wired or wireless manner) or indirectly via another device, e.g. via a patient monitor such as a conventional bedside patient monitor.

In still another embodiment the monitoring information providing device further comprises a food identification input for obtaining food consumption data identifying food consumed by the patient and the time, amount and/or route of consumption of the food by the patient, wherein said processing unit is configured to use the food consumption data in the determination of the expected changes of one or more physiological signs of the patient over time. Since also the consumption of food, e.g. before, during or after the administration of the drug (food not only has an effect if mixed with the drug, but may also have prolonged effects on metabolism and effect), may lead to drug-food interactions, this embodiment further improves the accuracy of the determination of the monitoring information.

In another embodiment the monitoring information providing device further comprises an alarm unit for generating and issuing an alarm in case a physiological sign indicated by the determined monitoring information reaches a critical state, wherein said alarm unit is configured to adapt its settings for determining if a physiological sign indicated by the determined monitoring information reaches a critical state based on the determined expected changes of one or more physiological signs of the patient over time. Thus, the number of false alarms can be substantially reduced, and critical alarms can be generated quicker.

Preferably, said patient data input is configured to obtain patient data of the monitored patient including the patient's profile, medical history, condition, disease state, co-morbidities, renal and hepatic function, current therapies including non-pharmacological treatments, blood values data and/or other examination data (e.g. imaging, histology of biopsies, etc.). This information may e.g. be obtained from medical records (e.g. EHR) or a hospital database, or may be inputted by the user via a user interface, e.g. a keyboard of a PC or the monitoring information providing device. The use of such information further improves the accuracy of the determination and dynamic adaptation of the monitoring information.

Advantageously, the proposed monitoring information providing device further comprises an imaging unit, in particular a camera, for providing image data, wherein said patient data input is configured to identify the patient from said image data (e.g. via face recognition) and/or said drug identification input is configured to identify the drug administered to the patient and the time of administration of the drug to the patient from said image data (e.g. via image processing to recognize an identifier attached to the drug container and to recognize the act of administration) and/or said processing unit is configured to determine one or more physiological signs of the patient from said image data (e.g. via the well-known remote photo-plethysmography technique) and to use the sensor signals in the determination of the monitoring information. This provides a simple and efficient way of determining the respective information.

However, other methods are applicable as well in the context of the present invention. For instance, a user interface (e.g. a keyboard or touchscreen) may be provided for entering patient data and/or drug data as well as the time of drug administration. Further, an appropriate reader may be used, such as an RFID reader or barcode scanner, for reading a corresponding identifier attached to the patient or patient bed for identifying the patient and/or attached to the drug container for identifying the drug. For measuring sensor signals related to physiological signs, corresponding sensors attached to the patient's body may be used, such as a pulse oximeter, SpO2 sensor, accelerometer (for motion detection and/or respiration rate detection), a breathing rate sensor, a temperature sensor, a blood pressure sensor, ECG electrodes, implantable devices, smart pills, nanotechnology based solutions, etc. Other methods such as sound processing can be used for patient identification and patient status information. Further, the proposed identifications can be done by other means as well, for example using wireless technologies (Wi-Fi, NFC) for patient identification, drug identification or food identification.

In still another embodiment, the monitoring information providing device further comprises an output device, in particular a display, loudspeaker, printer or transmitter, for providing the monitoring information to a user. Thus, the monitoring information may be directly outputted at the monitoring information providing device, or may be transmitted (in a wireless or wired manner, e.g. via Bluetooth, Wifi, UMTS, LAN, etc.) to a different device, e.g. a doctor's smartphone or tablet, a monitoring station in a nurse room, a patient monitor, a surveillance center for surveillance of patients at home, etc. The output, e.g. the displayed monitoring information, is preferably also dynamically adapted like the monitoring information itself.

Further, the different physiological signs may be highlighted or marked in different ways (color, font, etc.) based on how critical they are so that everyone looking at the monitor can immediately understand where to initially focus. The way of highlighting is preferably also changed over time depending on the dynamic adaption of the monitoring information.

In another embodiment a storage unit may be provided for storing the monitoring information, and optionally all data that have been outputted or displayed, so that the past time resolved physiological sign monitoring information can be easily accessed if necessary. This makes it possible to go back in time to see what kind of output has been produced earlier. For example, this may be used to check whether meaningful results are currently produced or if some data mining shall be made afterwards.

Further, in an embodiment a user interface may be provided for allowing a user to enter data into the device and/or for enabling a user, such as a specialized clinician or another expert, to access specific settings, where he can manually indicate which physiological signs should be critically monitored and when. In other words, an option may be given to the user to add more information, update the drug information input, or even to override the automatically determined monitoring information, e.g. automatically determined suggestions which physiological signs to monitor.

Still further, in an embodiment the device is configured to continuously learn and being adaptive. For example, if it is observed that patient A is sensitive to drug A, after the first administration of drug A, then this knowledge will be used how the critical physiological signs to monitor will be determined next time drug A is given. That is, this new information will be used to adapt the setting of the device, e.g. alarm thresholds, probabilities of adverse effects happening to this patient, etc.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
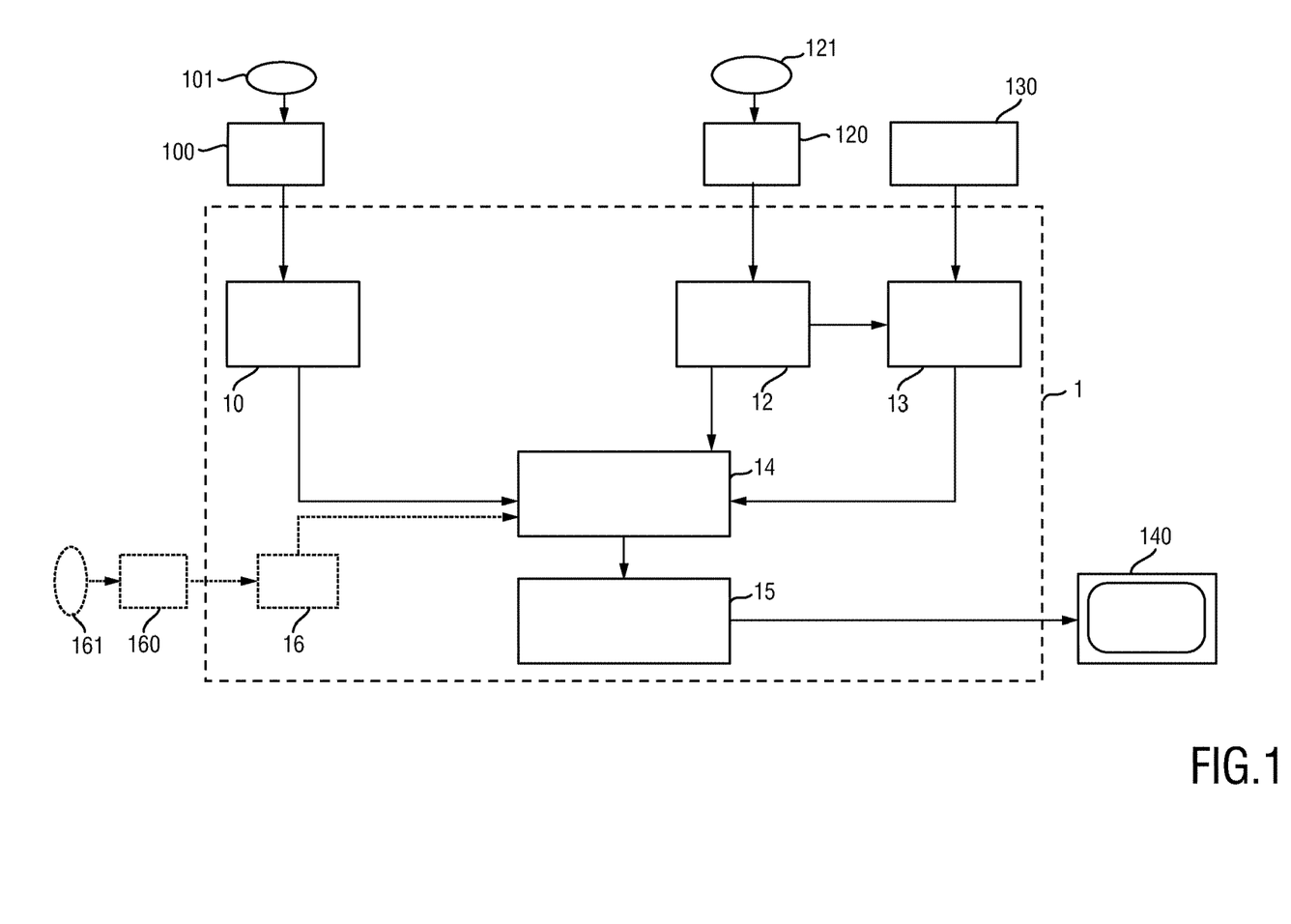
FIG. 1 shows a schematic diagram of a first embodiment of a monitoring information providing device according to the present invention.

FIG. 1 shows a schematic diagram of a first embodiment of a monitoring information providing device 1 according to the present invention. It comprises a patient data input 10 for obtaining patient data of a monitored patient 101, as e.g. provided from a patient data provider 100. A drug identification input 12 is provided for obtaining drug administration data identifying a drug 121 administered to the patient and the time of administration of the drug to the patient, as e.g. provided from a drug administration data provider 120. A drug information input 13 is provided for obtaining drug information of the identified drug (said identification information being included in the drug administration data), e.g. from an external database 130, said drug information including drug side effects and/or drug-drug interactions and/or drug-disease contraindications. Based on the obtained patient data, drug administration data (in particular the time of administration of the drug to the patient) and drug information a processing unit 14 determines time-resolved monitoring information, said monitoring information being dynamically adapted and indicating one or more physiological signs of the patient that are most critical to monitor over time. An output interface 15 outputs said monitoring information, e.g. to a display 140 for showing this information to a user, e.g. a caregiver, nurse or doctor and/or to a loudspeaker for acoustically issuing such information. This output is preferably made continuously or regularly, e.g. in accordance with the time rhythm in which the monitoring information is dynamically updated.

The monitoring information providing device 1 may generally be or integrated into a patient monitor as conventionally used, e.g. as bedside patient monitor. In other implementations the monitoring information providing device 1 may be a central computer or computer system, to which some or all of the various kinds of obtained data may be provided either directly or indirectly (e.g. via a conventional patient monitor) or a separate device. For the following explanation of the embodiment shown in FIG. 1 it shall be assumed that the monitoring information providing device 1 is stand-alone device that e.g. provides the monitoring information for controlling a patient monitor such as a bedside patient monitor, e.g. in a hospital or a nursing home.

In the following, exemplary implementations of the external elements 100, 120, 130 will be explained.

The patient data provider 100 may be implemented as a patient identification device, such as an RFID reader or a barcode reader, for reading a patient identifier (e.g. an RFID tag or barcode) attached e.g. to the patient or the patient bed and storing patient identification data (e.g. name, birthday, identification number, etc.). Further, the patient data provider 100 may include a patient database, e.g. an EHR or EMR, storing patient-related data such as the patient's profile, medical history, condition, disease state, co-morbidities, renal and hepatic function, current therapies including non-pharmacological treatments, blood values data and/or other examination data (imaging, histology of biopsies, . . . ) etc. All these patient data may then be provided to the monitoring information providing device via the patient data input 10, which is thus appropriately configured for obtaining these data. For instance, the patient data input 10 may comprise an interface for coupling a patient identification device to it, for receiving patient data of the identified patient from a remote patient database (e.g. via a (wired or wireless computer network), for entering patient data, etc.

The drug administration data provider 120 may be implemented, similar to the patient data provider 100, as a drug identification device, such as an RFID reader or a barcode reader, for reading a drug identifier (e.g. an RFID tag or barcode) attached e.g. to the container holding the drug or the package of the drug, said drug identifier storing drug identification data (e.g. the name of the drug, the producer, etc.).

The drug information input 13 is provided for obtaining drug information of the identified drug 121, e.g. from an external database 130 as for instance provided by the producer, a medical or pharmaceutical company, healthcare IT company, the distributor, the hospital, or another entity. Said drug database 130 holds drug information including drug effects, drug side effects, drug-drug interactions and/or drug-disease contraindications which are provided to the drug information input 13, which is thus appropriately configured for obtaining these data. For instance, the drug data input 12 may comprise an interface for accessing a remote drug database 130, e.g. via a (wired or wireless) computer network, communications network, the internet, in the cloud, etc. Alternatively, the drug database 130 may be held in the monitoring information providing device 1 itself.

In the following details of an exemplary use of this embodiment of the monitoring information providing device 1 shall be explained.

The barcode of the drugs is preferably scanned at the time of administration. In this way the exact time of drug administration is recorded and stored. Using this information a timeline of the expected course of adverse effects will be automatically calculated by accessing the drug, drug-drug interaction, drug-disease contraindications and patient data.

Patients can be also scanned before drug administration (e.g. from identification bracelet IDs, passports, facial recognition etc.) and their medical history may be used to calculate patient-adapted timelines of expected interaction and physiological signs to monitor.

In addition, measured or calculated physiological signs can be used to automatically assign the patient to predefined patient groups, which can then be used to fine tune the patient-group adapted timeline of expected interactions. Assuming there is a database of physiological signs and drug information, automatic parameter classification algorithms (such as k-means, neural networks, Hidden Markov Models, etc.) can be used to learn how the physiological signs are changing with respect to certain drug. For example, for a drug A, using the historical data, the physiological signs data before drug intake can be used to generate clusters of condition before drug intake, such as PreCluster1, PreCluster2, etc. Similarly clusters for after drug intake, such as PostCluster1, PostCluster2, PostCluster3, can be generated. Using the calculated clusters, for each drug or combination of drugs the likelihood of moving from one PreCluster to one PostCluster can be calculated. Using this algorithm, for a patient without any identification or medical history data, the physiological signs can be monitored for specific amount of time (for example 30-60 min, or less when applicable). This data may then be used to assign a patient into one of the PreClusters. Then the monitoring information providing device and method can be used as described above. For a patient with historical physiological signs information, the historical data and the current measured data are preferably used to determine the PreClusters, and the PostClusters, and also the likelihood of moving from one PreCluster to one PostCluster. Depending on the observed patient condition, the Pre- and Post-clusters may be dynamically adapted.

In one embodiment of the monitoring information providing device, a food identification input 16 (shown in FIG. 1 as optional element) may be provided for obtaining food consumption data identifying food consumed by the patient and the time, amount and/or route of consumption of the food by the patient. Thus, similar to the drugs, food 161 can be also identified, e.g. by use of a food data provider 160 which may also be a barcode scanner or RFID reader (or even the same device as the drug administration data provider 120). This information can then be used to predict potential drug-food interactions, the expected adverse effects, their time course, and physiological signs to be monitored.

In a preferred embodiment a limited number of critical physiological signs to monitor may be highlighted, e.g. on the display 140, according to the calculated timeline. This will serve as a reminder to the attending staff and provide support in drawing the attention of the attending staff to the particular important information to monitor. Additionally, if space on the displayed screen allows, the drug(s) that cause the potential adverse effect and, optionally, further drug information on these drugs, may be displayed. This information may be updated based on the expected time course of the evolution of the adverse effect and may be removed when the critical period has passed.

Figure 2:
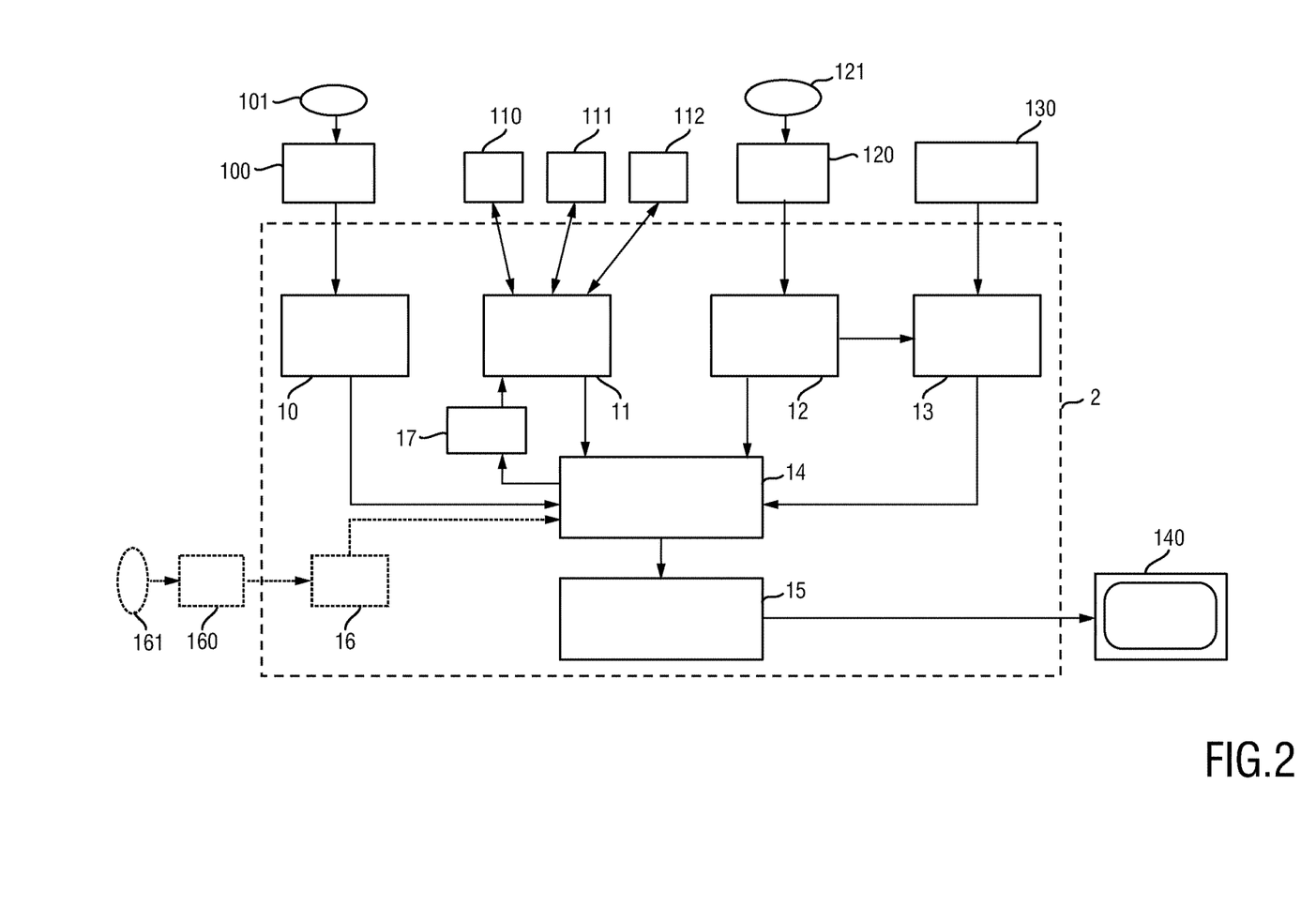
FIG. 2 shows a schematic diagram of a second embodiment of a monitoring information providing device according to the present invention.

FIG. 2 shows a schematic diagram of a second embodiment of a monitoring information providing device 2 according to the present invention. In addition to the elements shown in FIG. 1 a sensor interface 11 is provided for obtaining one or more sensor signals related to one or more physiological signs of the patient, as e.g. provided from one or more sensors 110, 111, 112. In this embodiment the processing unit 14 determines the monitoring information based on the sensor signals (and/or physiological signs derived there from) in addition to the obtained patient data and drug information.

The sensors 110, 111, 112 may be separate body-mountable (controllable and/or non-controllable) sensors that are generally attached to the patient's body for measuring sensor signals related to physiological signs of the patient, i.e. which are directly representing a physiological sign (e.g. the temperature obtained from a thermometer) or a used to retrieve a physiological sign (e.g. an ECG signal from which the pulse rate can be retrieved). Examples of such sensors include pulse oximeters, SpO2 sensors, accelerometers (for motion detection and/or respiration rate detection), breathing rate sensors, temperature sensors, blood pressure sensors, ECG electrodes, etc.

The second embodiment shown in FIG. 2 may also be stand-alone device or integrated into another device. The monitoring information providing device 2 together with the external elements 100, 110-112, 120, 130, 140 may also be regarded as a monitoring information providing system.

Further, alterations of the settings of the monitoring information providing device 1 or 2 and/or of any external elements (as e.g. shown in FIG. 1 or 2) connected to the monitoring information providing device 1 or 2 may be made based on the determined monitoring information. For instance, based on the expected critical physiological signs the alert settings for physiological signs sensors (e.g. vital signs sensors), camera-interpreted behavior monitors, or other monitoring devices may be altered automatically.

For instance, a control unit 17 may be provided for generating control information for controlling one or more of the external sensors 110, 111, 112 via the sensor interface 11 to adapt the measurements made by the one or more sensors 110, 111, 112 based on the determined expected changes of one or more physiological signs of the patient over time. For instance, the one or more sensors may be controlled to start measurement, to perform measurement for a particular time period, to change the measurement frequency and/or to adapt other settings of the measurement based on the determined expected changes of one or more physiological signs of the patient over time. Surpassing the levels of the current flagged physiological signs may also trigger a higher alert level than normal.

Moreover, the monitoring information providing device 1 or 2 may display instructions for additional monitoring information providing, e.g. to attach pulse oximeter, determine blood pressure every five minutes, check for skin conditions, ask the patient if he feels more pain than usual, which should be followed by the attending staff. Additionally or alternatively, the monitoring information providing device 1 or 2 may also automatically initiate or change parameters of any elements of the system, such as the measurement frequency of selected sensors or physiological monitors (e.g. automated cuff blood pressure devices).

Figure 3:
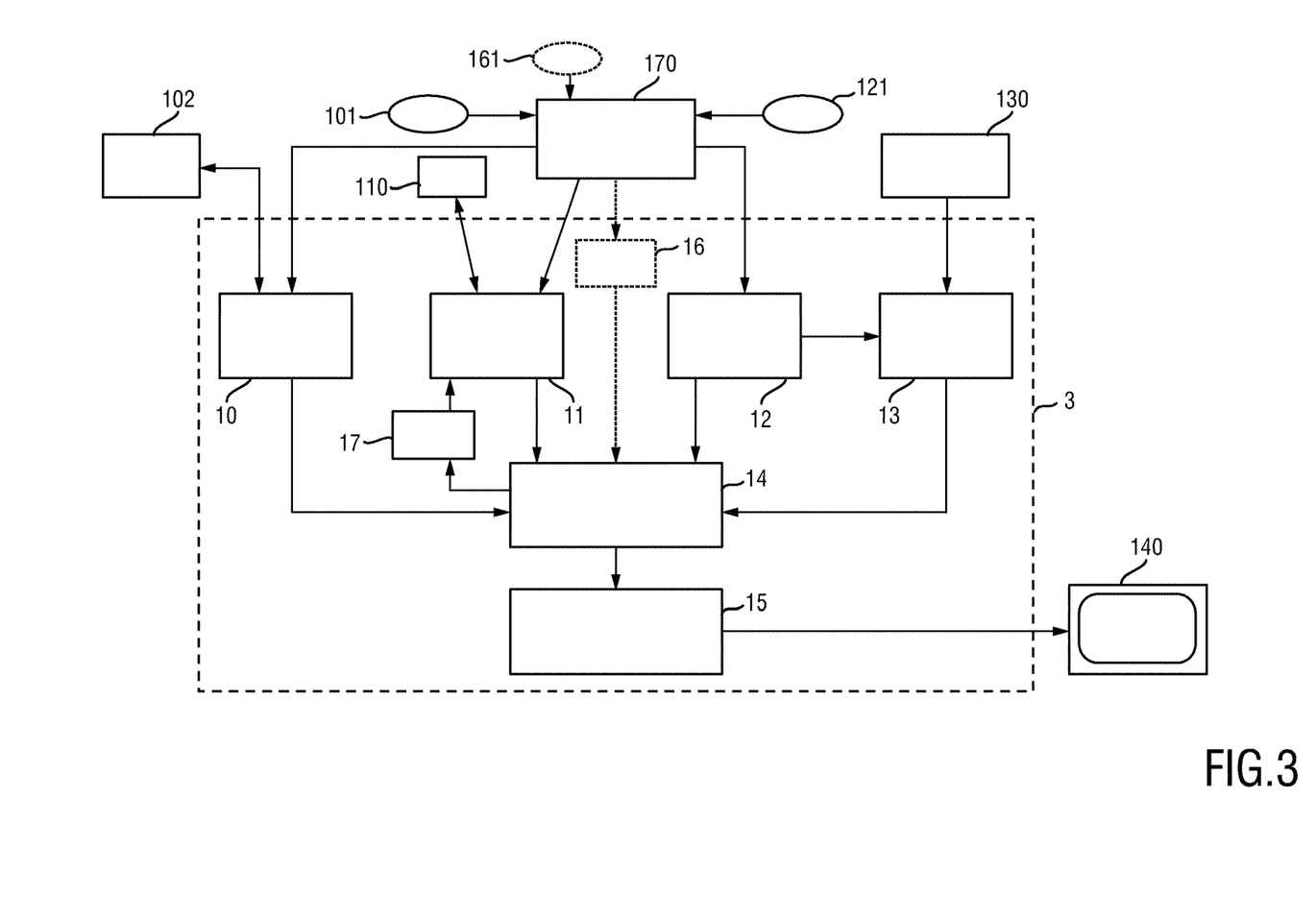
FIG. 3 shows a schematic diagram of a third embodiment of a monitoring information providing device according to the present invention.

FIG. 3 shows a schematic diagram of a third embodiment of a monitoring information providing device 3 according to the present invention. In this embodiment an imaging unit 170, such as a camera, is provided which takes over the tasks of several of the external elements shown in FIG. 1 or 2.

In particular, the imaging unit 170 may replace at least part of the patient data provider 100 by identifying within one or more acquired images the patient 101, either directly by use of a person recognition algorithm, e.g. face recognition, or indirectly by identifying a tag (e.g. a barcode or name tag) attached to the patient or somewhere near the patient. This identification can e.g. be made by the imaging unit 170, the patient data input 10 or the processing unit 14. Other patient data, like the patient profile, the medical history, current patient status, etc. may either be available within the monitoring information providing device 1 or 2 or may be retrieved by the patient data input 100 from a database 102, e.g. the hospital's patient database.

Further, the imaging unit 170 may replace the drug administration data provider 120 by identifying within one or more acquired images the drug 121, either directly by use of a drug recognition algorithm, e.g. sample or package recognition, or indirectly by identifying a tag (e.g. a barcode or name printed on the drug container or the package). This identification can e.g. be made by the imaging unit 170, the drug data input 12 or the processing unit 14.

Optionally, the imaging unit 170 may replace the food data provider 160 by identifying within one or more acquired images the food 160, either directly by use of a food recognition algorithm, e.g. sample or package recognition, or indirectly by identifying a tag (e.g. a barcode or name printed on the food container or the package). This identification can e.g. be made by the imaging unit 170, the food data input 16 or the processing unit 14.

Still further, the imaging unit 170 may replace one or more of the sensors 110, 111, 112. For instance, heart rate, SpO2 and respiration rate can be derived from a time series of images of the patient by use of the well-known remote photo-plethysmography (remote PPG) technology so that corresponding body-mounted sensors can be replaced. Other sensors, like a blood pressure sensor 110, may, however, not easily be replaced. The determining of physiological signs of the patient from the images may either be performed directly within the imaging, but is preferably performed by either the sensor interface 11 or the processing unit 15 (or an additional separate unit not shown in FIG. 2) is configured to determine one or more physiological signs of the patient from said image data.

Figure 4:
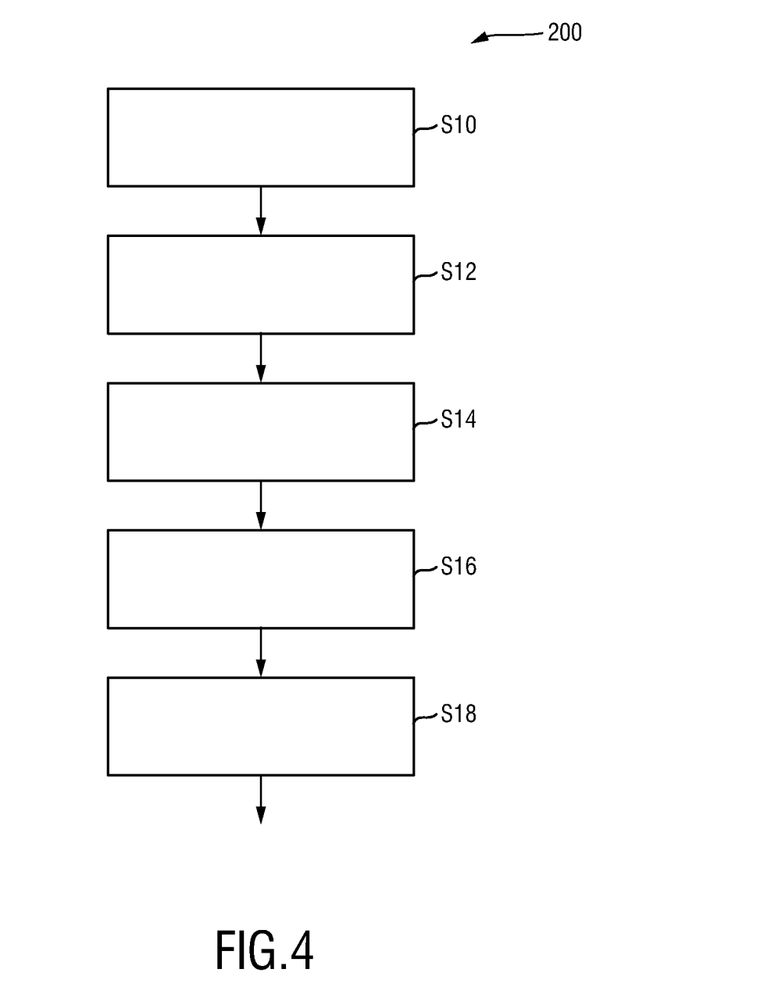
FIG. 4 shows a flow chart of an embodiment of a monitoring information providing method according to the present invention.

A flow chart of an embodiment of the proposed monitoring information providing method 200 is shown FIG. 4. In a first step S10 patient data of a monitored patient are obtained. In a second step S12 drug administration data identifying a drug administered to the patient and the time of administration of the drug to the patient are obtained. In a third step S14 drug information of the identified drug are obtained, said drug information including drug side effects and/or drug-drug interactions and/or drug-disease contraindications. In a fourth step S16 monitoring information is determined based on the obtained patient data, drug administration data and drug information. In a fifth step S18 the determined monitoring information is outputted. This monitoring information providing method may have further embodiments and options similar as explained above with respect to the monitoring information providing device. Further, the chronological sequence of the first three steps S10, S12, S14 may also be different, e.g. the second and third steps S12, S14 may be performed before the first step S10.

Figure 5:
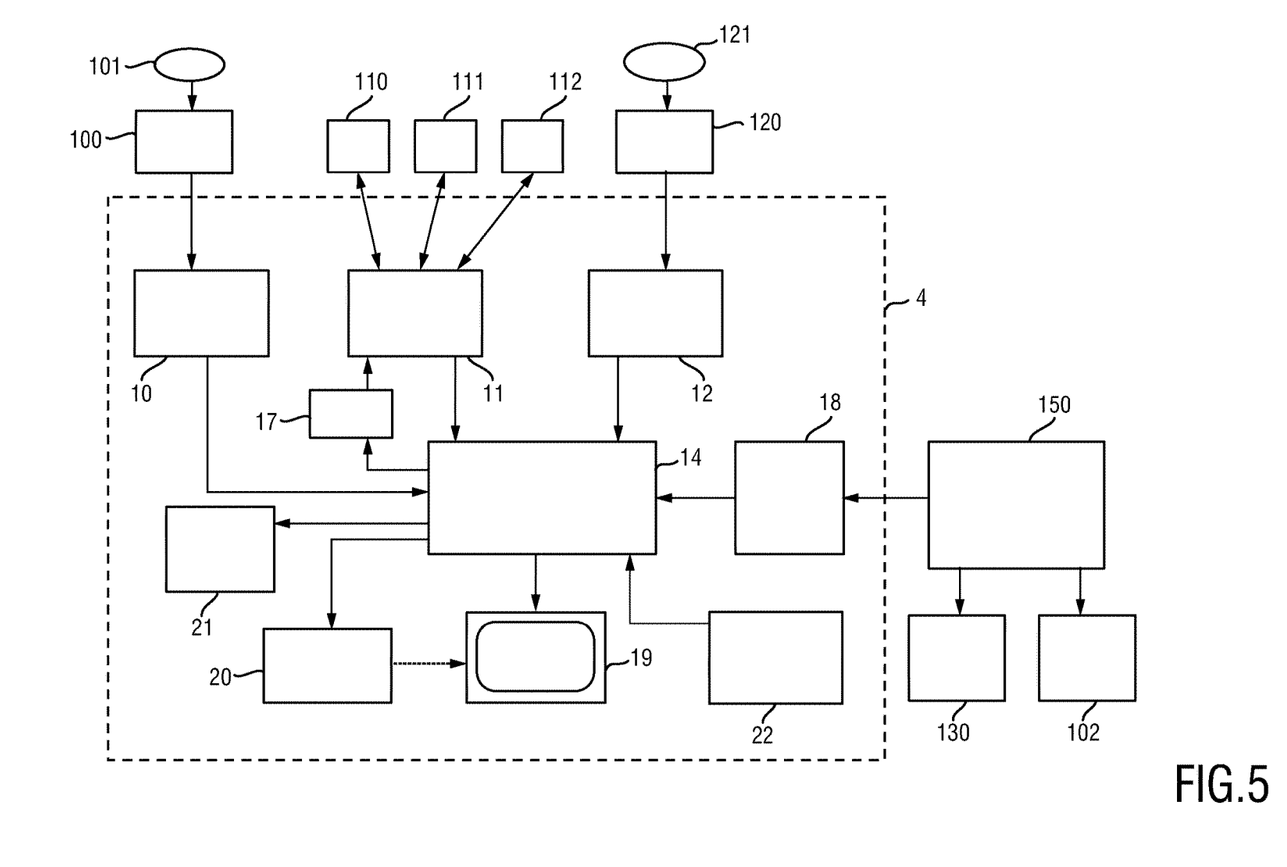
FIG. 5 shows a schematic diagram of a fourth embodiment of a monitoring information providing device according to the present invention.

FIG. 5 shows a schematic diagram of a fourth embodiment of a monitoring information providing device 4 according to the present invention. Many of the elements provided in the first and second embodiments as shown in FIGS. 1, 2 and 3 are provided in this embodiment as well. However, part of the tasks of the patient data input 10 and/or the drug information input 13 are performed by a common data input 18. This data input 18 is coupled to an external system 150, which may be an external computer system, e.g. of the hospital computer system, or a central workstation, or an external personal computer. This external system 150 is able to access one or more databases to retrieve information required by the monitoring information providing device 4. In particular, the patient database 102 (e.g. within the hospital network, or stored at an external medical data provider, or one or more external doctors) may be accessed to retrieve patient data for the identified patient. Further, a drug database 130 may be accessed to obtain drug information for the identified drug. Still further, a food database (not shown) may be accessed optionally, if food intake is also identified by the monitoring information providing device.

The external system 150 may also take over further tasks, e.g. the task of patient identification, drug identification and/or food identification based on image data (if such are available as in the third embodiment of the monitoring information providing device 3) by use of image processing or the task of calculating patient-related alarm limits for physiological signs to be monitored, etc.

The monitoring information providing device 4 may be designed like a conventional monitoring information providing device and may include a monitor 19, representing the output interface. Generally, other additional information apart from the information mentioned above may be displayed, such as calculated health scores, ECG curves, patient data, warnings, etc. Further, an alarm unit 20 may be provided for generating and issuing an alarm (e.g. visually and/or audible) in case a physiological sign reaches a critical state. Preferably, said alarm unit 20 is configured to adapt its settings (or is being controlled to adapt its settings) for determining if a physiological sign reaches a critical state based on the determined expected changes of one or more physiological signs of the patient over time. Such alarms (and optionally the settings) may also be displayed on the monitor 19.

Further, a storage unit 21 may be provided for storing the monitoring information, and optionally all data that have been outputted or displayed, so that the time resolved physiological signs feedback can be easily accessed if necessary.

Still further, a user interface 22 may be provided for allowing a user to enter data into the device and/or for enabling a user, such as a specialized clinician or another expert, to access specific settings, where he can manually indicate which physiological signs should be critically monitored and when. In other words, the user to add more information or even to override the automatically determined monitoring information, e.g. automatically determined suggestions which physiological signs to monitor.

In the following some detailed examples of how the invention may be used in practice will be explained. The examples are set in the highly monitored environments of an ICU (intensive care unit) or ER (emergency room). However, with the advent of ubiquitous and less invasive monitoring the required level of monitoring may become available in the general ward of the hospital, nursing homes and maybe even in the home situation within the foreseeable future.

In the ICU antibiotics are commonly used to prevent or treat infections. However, antibiotics of the penicillin and cephalosporin class carry a risk of allergic reactions. Especially with intravenous administration and in ICU patients this may be life-threatening. Serious allergic reactions (anaphylaxis) can have a very quick onset of seconds to minutes upon start of administration, and require immediate medical treatment. They may occur the first time a patient ever receives the drug, but also even after the patent has been given the drug before without any problems. Life-threatening anaphylactic shock presents itself mainly as a drop in blood pressure which then triggers a reflex increased heart rate, and/or edema in the respiratory tract causing respiratory distress, followed by loss of consciousness and occasionally death. Other effects will present themselves as well but are less life-threatening.

In a first example a patient shall be considered who will receive penicillin by infusion. Depending on the rate of the IV (intravenous) drip it may take less than a minute up to five minutes before the drug enters the patient's bloodstream. Ideally, a nurse, or even better a doctor, would continuously monitor the patient for the first 15 minutes, but this is often impossible in daily practice. Rather, the attending nurse will try to give extra attention to the patient while doing other tasks, but may also be distracted by other medical urgencies. In case of abnormal physiological signs the nurse will interpret the situation and taking appropriate action if needed, and alert the doctor, but not all nurses will be able to interpret every situation.

To give a practical example, a feedback from a practicing medical doctor regarding the aforementioned statement is the following: "Yes, very true. There may also be an advantage of detecting an early trend, or combination of trends. A nurse (who is ultimately the person administrating the drug) does not always have the knowledge to interpret physiological signs. Keeping a doctor at the bedside is too expensive." Such situations can e.g. be improved by use of the present invention as follows.

At time of hooking up the penicillin to the infusion system, the barcode of the IV bag with antibiotics is scanned, as well as the identification tag of the patient and/or the patient monitor.

The medication alert system will check for a pre-existing penicillin allergy for this patient and issue a medication alert, e.g. at a central monitor (e.g. at the pharmacy or at the central nurse station), if this is found. Current systems already have this functionality, however often the medication info is added to the patient file only after administration and/or at a central station in the department, so that the alarm is generated too late. The proposed monitoring information providing device, however, may in addition also display this alert on the display at the monitoring information providing device and/or give an auditory alarm at the monitoring information providing device, i.e. right at the patient's location. Conventionally, the drug information is often entered into the system at a central location (pharmacy, central nurse station). The present invention provides the functionally of doing this at the patient side, which also means that alarms can be also displayed on the patient monitors as well as central monitors.

If no data on pre-existing penicillin allergy is found, the proposed monitoring information providing device will display on the display at the monitoring information providing device the three main physiological signs of a life-threatening anaphylactic reaction that currently need to be checked with priority, i.e. increased heart rate, decreased blood pressure and respiratory difficulty. In addition to these, when available, temperature measurements and skin reactions can be also analyzed and taken into account. For example, since skin reactions are present in 90% of the anaphylactic situations, the information displayed at the monitoring information providing device can include suggestions for these checks.

Such information may also be presented for 15 minutes. After this time the risk of serious side effects for this medication administration is gone, and maintaining the information on the screen will only distract staff.

In addition, the proposed monitoring information providing device will advise high frequency blood pressure measurements (every minute if possible) for the coming 15 minutes, or initiate these if automatic blood pressure devices are in place.

If during the 15 minutes heart rate is increased above threshold level or shows a significant upward trend compared to the previous 10 minutes, blood pressure drops below threshold level or shows a downward trend, or breathing pattern shows irregularities compared to the previous 10 minutes, a high level/priority alert is triggered—patient is likely in immediate mortal danger and requires immediate attention.

After 15 minutes the proposed monitoring information providing device resets to normal. The information on the display at the monitoring information providing device is removed, automatic high frequency blood pressure measurements—if initiated—are set back to normal frequency, physiological signs are no longer monitored for trend—unless this was already the case—and violations of threshold levels will trigger normal alarms, not high level priority alarms.

Although the example is for penicillin, a similar chain of events can be set for other drugs that have an increased risk of inducing anaphylaxis, such as blood infusions and blood products, NSAIDs, morphine and vancomycine.

In the following a second example shall be given. Olanzapine is an antipsychotic, used to treat schizophrenia and sometimes also to decrease acute agitation. Use of benzodiazepines such as valium is also common in these patients, however combined the two may lead to severe hypotension, oversedation, cardiorespiratory depression, which has been on occasion fatal. After an intramuscular injection of olanzapine a doctor should not give injections of valium for at least one hour. A patient who has been given valium should only be given intramuscular olanzapine under close monitoring.

In the second example an agitated patient shall be considered who is brought into the ER. The patient is given haloperidol but does not respond. Next, the patient receives an intramuscular injection of olanzapine. Of both drugs the barcode is read at time of administration. The patient responds only partially and later on the patient is given an injection of valium, which is also entered into the monitoring information providing device by reading of the barcode.

Several scenarios are possible. In a first scenario the valium is given more than 1 hour after the olanzapine. In this case no alert is created.

In a second scenario the valium is given within one hour after the olanzapine. In this case an alert may be created on a central monitor of the system. This comprises which drugs are involved and the adverse effect which may be expected. In addition the monitoring information providing device may also create an alert on the bedside monitor of the patient, stating the three main physiological signs to watch: lowered blood pressure, lowered breathing frequency, severely lowered consciousness level. A nurse or doctor who notices a change in these physiological parameters will raise an alarm so that appropriate action is taken, even if they do not know the particular situation of this patient, or do not know the exact interaction effects of this particular drug-drug interaction. After a set amount of time, e.g. two hours, these physiological signs are automatically removed, as there is no longer an immediate danger from these medications.

In the third scenario the valium is given within one hour, but in addition a friend of the patient who came by has given the information that the patient has had alcoholic drinks that evening. This information is also entered into the monitoring information providing device. In this case a higher level priority alarm is generated and the monitoring information providing device advises to attach a pulse-oximeter to monitor blood oxygenation, if not already present. Further, on the monitor at the monitoring information providing device the same three main physiological signs may be listed. In addition, the monitoring information providing device automatically sets a more stringent alarm level to the blood oxygenation level, and if it drops below this threshold a high level priority alert will be generated at the monitoring information providing device and the nurse's station, as the patient is likely going into respiratory distress.

In summary, the present invention proposes to generate and output, in particular display, dynamically adapting information on a monitoring information providing device, which information is changing based on expected adverse reactions due to drug side effects, drug-drug interactions or drug-disease contraindications. The outputted information is time-resolved, which means that the data is updated following the time course of the potential adverse effects, and comprises the most important physiological signs to pay attention to.

The benefits of the invention are that it makes the outputted physiological sign information and consequently the alarms more relevant to the patients' condition. If desired this information can be used to prioritize the alarms and adapt the alarm thresholds dynamically.

In addition to outputting drug-related information, the proposed monitoring information providing device can automatically initiate additional measurements—such as blood pressure—in a time-resolved manner, according to the times when pivotal changes (e.g., in blood pressure) are expected.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A monitoring information providing device comprising:
 a plurality of sensors configured to measure a plurality of physiological signs of a monitored patient;
 a bedside patient monitor configured to control the sensors to measure each of the plurality of the physiological signs with a selected measurement frequency;
 a drug label reader configured to obtain drug administration data identifying a drug administered to a patient and a time of administration of the drug to a patient; and
 one or more processors configured to:
  retrieve medical data of the monitored patient from a patient database,
  determine drug information of the identified drug, said drug information including drug side effects, and/or drug-drug interactions and/or drug-disease contraindications, and/or drug-food interactions, determine how the potential drug side effects, and/or the drug-drug interactions, and/or the drug-disease contraindications and/or the drug-food interactions are expected to cause changes of physiological signs, to which extent changes are expected and/or how critical the respective changes are, determine changes in the monitored physiological signs that are expected due to the administered drug, determine at what time changes of physiological signs due to the administered drug are expected, compare the measured physiological signs with corresponding thresholds to determine how critical the respective changes in the monitored physiological signs are, and control the patient monitor to dynamically adapt at least one of the thresholds and the selected measurement frequency for a time based on the determined time at which the physiological signs are expected and based on the expected changes, the criticality of the respective changes, drug-drug interactions, drug-disease contraindications and/or drug-food interactions.

2. A monitoring information providing device comprising:

a plurality of sensors configured to measure a plurality of physiological signs of a monitored patient;

a bedside patient monitor configured to control the sensors to measure each of the plurality of the physiological signs with a selected measurement frequency to compare the measured physiological signs with corresponding thresholds, a barcode or RFID reader disposed adjacent the monitored patient and configured to read a medicine identifying label of a container containing a drug being administered to the patient and determine an administration time when the label is read;

one or more processors configured to:
retrieve medical data of the monitored patient from a patient database,
retrieve drug information for the identified drug from a drug database, the drug information including drug side effects and/or drug-drug interactions and/or drug-disease contraindications,
determine at what time changes of physiological signs due to the administered drug are expected,
determine changes in the monitored physiological signs that are expected due to the administered drug,
determine how critical the respective changes in the monitored physiological signs are,
determine potential drug side effects, drug-drug interactions, drug-disease contraindications and/or drug-food interactions may appear due to the administered drug,
determine how these potential drug side effects, drug-drug interactions, drug-disease contraindications and/or drug-food interactions are expected to cause changes of physiological signs, to which extent changes are expected and/or how critical the respective changes are, and
control the bedside patient monitor to change at least one of the thresholds and the selected measurement frequency for a time based on the determined time at which the physiological signs are expected and based on the expected changes, the criticality of the respective changes, and the potential drug side effects, drug-drug interactions, drug-disease contraindications and/or drug-food interactions may appear.

3. The monitoring information providing device as claimed in claim 1, further comprising:

a plurality of sensors configured to monitor physiological signs of the patient; and a sensor control configured to control the sensors, which provide sensor signals related to the monitored physiological signs that have been determined to be most critical to monitor, to adapt the measurements made by the sensors based on the determined monitoring information.

4. The monitoring information providing device as claimed in claim 3, wherein said sensor control is configured to control the sensors to perform measurement for a particular time period, to change the measurement frequency and/or to adapt other settings of the measurement based on the determined monitoring information.

5. The monitoring information providing device as claimed in claim 1, wherein the drug label reader is disposed adjacent the patient and configured to obtain the drug administration data contemporaneously with the administration of the drug, the drug administration data further including the route of administration and/or the amount of the drug administered to the patient.

6. The monitoring information providing device as claimed in claim 1, wherein the one or more processors are further configured to obtain further drug administration data identifying one or more further drugs that have been administered earlier or that will be administered later to the patient and the time of administration of the one or more further drugs, and use the further drug administration data in the determination of the monitoring information.

7. The monitoring information providing device as claimed in claim 6, wherein the one or more processors are configured to obtain further drug administration data further including the route of administration and/or the amount of the one or more further drugs.

8. The monitoring information providing device as claimed in claim 1, wherein the one or more processors are further configured to:

obtain food consumption data identifying food consumed by the patient and a time, amount and/or route of consumption of the food by the patient, use the food consumption data in the determination of the monitoring information.

9. The monitoring information providing device as claimed in claim 1, wherein the one or more processors are further configured to:

control an alarm to issue an alarm in case a physiological sign indicated by the determined monitoring information reaches a critical state, wherein said alarm is configured to adapt its settings for determining if a physiological sign indicated by the determined monitoring information reaches a critical state based on the determined monitoring information.

10. The monitoring information providing device as claimed in claim 1, wherein the obtained patient data includes the patient's profile, medical history, condition, disease state, co-morbidities, renal and hepatic function, current therapies including non-pharmacological treatments, blood values data and/or other examination data.

11. The monitoring information providing device as claimed in claim 1, further comprising:

a sensor interface configured to obtain one or more sensor signals related to one or more physiological signs of the patient, wherein said one or more processors are configured to use the sensor signals in the determination of the monitoring information.

12. The monitoring information providing device as claimed in claim 1, further comprising:
a camera configured to provide image data, and wherein the one or more processors are further configured to:
identify the patient from said image data and/or
identify the drug administered to the patient and the time of administration of the drug to the patient from said image data and/or
determine one or more physiological signs of the patient from said image data and use the determined physiological signs in the determination of the monitoring information.

13. The monitoring information providing device as claimed in claim 1, further comprising:
a display, loudspeaker, printer or transmitter, for providing the monitoring information to a user.

14. A monitoring information providing method comprising:
with a plurality of sensors, measuring a plurality of physiological signs of a monitored patient;
with a bedside patient monitor, monitoring selected physiological signs of a patient with the sensors with at least one of the monitored physiological signs being monitored at a selected measurement frequency, and comparing values of the monitored physiological signs with selected thresholds,
with a barcode or RFID reader disposed adjacent the monitored patient, reading a medicine identifying label of a container containing a drug being administered to the patient and determine an administration time when the label is read,
obtaining patient data of the monitored patient from a medical records database,
obtaining drug information of the identified drug, said drug information including drug side effects and/or drug-drug interactions and/or drug-disease contraindications and including changes in the physiological signs and expected durations of the changes,
determining changes in the monitored physiological signs that are expected due to the administered drug,
determining at what time changes of physiological signs due to the administered drug are expected,
determining how critical the respective changes in the monitored physiological signs are,
determining potential drug side effects, drug-drug interactions, drug-disease contraindications and/or drug-food interactions may appear due to the administered drug,
determining how these potential drug side effects, drug-drug interactions, drug-disease contraindications and/or drug-food interactions are expected to cause changes of physiological signs, to which extent changes are expected and/or how critical the respective changes are, and
controlling the bedside patient monitor to change at least one of the thresholds and the selected monitoring frequency for a time based on the determined time at which the physiological signs are expected and based on the expected changes, the criticality of the respective changes, and the potential drug side effects, drug-drug interactions, drug-disease contraindications and/or drug-food interactions may appear.

15. A non-transitory computer-readable medium carrying program code which, when performed on a computer causes the computer to carry out the steps of the method as claimed in claim 14.

16. The monitoring information providing device as claimed in claim 2, wherein the sensor controller, the barcode reader, and the one or more processors are incorporated into a bedside patient monitor.

17. The monitoring information providing device as claimed in claim 2, wherein the one or more processors are further configured to generate a timeline of an expected course of adverse physiological sign effects and control the sensor controller to change the thresholds and measurement frequency during the timeline and relinquish control of the sensor controller at the end of the timeline.

18. The monitoring information providing device as claimed in claim 2, wherein the drug includes an antibiotic which, in some patients, induces a serious anaphylactic reaction within seconds of starting the administration of the drug.

19. The monitoring information providing device as claimed in claim 18, wherein the one or more processors are configured to control the sensor control to monitor blood pressure more frequently, monitor heart trends of decreasing blood pressure and increasing heart rate, and in response to the decreasing blood pressure and/or increasing heart rate, causing a monitor or alarm to warn of potentially impending anaphylaxia.

20. The monitoring information providing device as claimed in claim 19, wherein the one or more processors control the sensor control to change at least one of the thresholds and the selected measurement frequency for a time of 15 minutes or less.

* * * * *